(12) United States Patent
Agarwal et al.

(10) Patent No.: US 10,016,345 B2
(45) Date of Patent: Jul. 10, 2018

(54) KIT FOR WHITENING A BODY SURFACE OF A USER, RELATED METHOD AND PROCESS

(71) Applicant: L'OREAL, Paris (FR)

(72) Inventors: Gaurav Agarwal, Rajasthan (IN); Shoibal Pattanaik, Westbengal (IN); Prasun Bandyopadhyay, Bangalore (IN); Caroline Delaunay, Shanghai (CN)

(73) Assignee: L'OREAL, Paris (FR)

( * ) Notice: Subject to any disclaimer, the term of this patent is extended or adjusted under 35 U.S.C. 154(b) by 359 days.

(21) Appl. No.: 14/906,676

(22) PCT Filed: Jul. 15, 2014

(86) PCT No.: PCT/EP2014/065125
§ 371 (c)(1),
(2) Date: Jan. 21, 2016

(87) PCT Pub. No.: WO2015/010955
PCT Pub. Date: Jan. 29, 2015

(65) Prior Publication Data
US 2016/0158123 A1 Jun. 9, 2016

(30) Foreign Application Priority Data
Jul. 22, 2013 (IN) .......................... 2178/DEL/2013

(51) Int. Cl.
*A61K 8/02* (2006.01)
*A61K 8/22* (2006.01)
(Continued)

(52) U.S. Cl.
CPC ............. *A61K 8/22* (2013.01); *A45D 44/002* (2013.01); *A61K 8/0208* (2013.01);
(Continued)

(58) Field of Classification Search
CPC ........ A61K 8/22; A61K 8/0212; A61Q 19/02; A45D 44/002
(Continued)

(56) References Cited

U.S. PATENT DOCUMENTS

2004/0191299 A1* 9/2004 Hinotani ............. A61K 8/0212
424/443
2004/0267190 A1* 12/2004 Tamarkin ............. A61K 9/0009
604/20

(Continued)

FOREIGN PATENT DOCUMENTS

DE 102010048408 A1 4/2012
WO WO-2012/153336 A2 11/2012

*Primary Examiner* — Susan Su
(74) *Attorney, Agent, or Firm* — Polsinelli PC

(57) ABSTRACT

Kit for whitening a body surface of a user, comprising:
an oxidizing composition application device (12);
wherein the kit comprises an activator sheet (14) which is movable independently of the oxidizing composition application device (12), the activator sheet (14) comprising an outer deformable substrate (50) intended to be applied on an oxidizing composition (34) placed on the skin of the user, the activator sheet (14) comprising an activator composition (52) carried by the outer substrate (50).

20 Claims, 3 Drawing Sheets

(51) Int. Cl.
  *A45D 44/00* (2006.01)
  *A61Q 19/02* (2006.01)
  *A61K 8/23* (2006.01)

(52) U.S. Cl.
  CPC .............. *A61K 8/0212* (2013.01); *A61K 8/23* (2013.01); *A61Q 19/02* (2013.01); *A61K 2800/884* (2013.01)

(58) Field of Classification Search
  USPC ....................................................... 604/303
  See application file for complete search history.

(56) References Cited

U.S. PATENT DOCUMENTS

| | | | |
|---|---|---|---|
| 2008/0014231 A1* | 1/2008 | Okano | A61K 8/0208 424/401 |
| 2008/0083420 A1 | 4/2008 | Glenn et al. | |
| 2009/0280150 A1* | 11/2009 | Kamen | A45D 34/04 424/401 |
| 2010/0228204 A1* | 9/2010 | Beatty | A45D 44/002 604/303 |
| 2011/0300196 A1* | 12/2011 | Mohammadi | A45D 44/002 424/401 |
| 2012/0195941 A1 | 8/2012 | Busch et al. | |
| 2013/0255713 A1 | 10/2013 | Schnitzler et al. | |
| 2017/0251789 A1* | 9/2017 | Kim | A45D 44/002 |

* cited by examiner

KIT FOR WHITENING A BODY SURFACE OF A USER, RELATED METHOD AND PROCESS

CROSS REFERENCE TO RELATED APPLICATIONS

This application is a National Phase filing under 35 U.S.C. § 371 of PCT/EP2014/065125 filed on Jul. 15, 2014; and this application claims priority to Application No. 2178/DEL/2013 filed in India on Jul. 22, 2013 under 35 U.S.C. § 119. The entire contents of each application are hereby incorporated by reference.

The invention concerns a kit for whitening a body surface of a user.

The color of skin is mainly determined by melanin, a pigment synthesized in melanocytes which are found in the basal layer of the epidermis. The melanin content of the skin defines the intensity of its darkness.

In some instances, it is desired to lighten the skin at least locally, e.g when the distribution of the melanin in skin is heterogeneous (for example in freckles and in moles) or more generally, in case the skin is homogeneously dark.

Different kinds of whitening agents with different skin whitening mechanism are well known. For example, kojic acid interferes with the synthesis of melanin in the melanocytes of the skin, therefore reducing the total amount of melanin in the skin.

Some exfoliates such as ascorbic acid, salicylic acid and lactic acid, have also been used as whitening agents.

Some yeast extract or live yeast belonging to the genus *Saccharomyces* has also been known to exhibit a melanin decomposing effect.

Further, some bleaching agents such as hydrogen peroxide, hydroquinone, 4-isopropylcatheol and hydroquinone monobenzyl ether, lighten the skin by decomposing melanin in the skin.

The mechanism behind whitening of skin can be the decomposition of hydrogen peroxide into water and free oxygen. The free oxygen is responsible for whitening of skin.

In cosmetics, this mechanism is used for whitening of skin and hair. Generally, in such applications, hydrogen peroxide is used at very low concentrations, e.g. 3-4%.

Hydrogen peroxide has also been proposed for skin therapy and wound management, principally for its beneficial oxidative properties such as disclosed in U.S. Pat. Nos. 6,673,374; 6,117,118; 5,879,716; 5,653,994; and 4,826,681.

Skin whitening products are generally sold in two separately packed preparations, comprising a bleaching cream and an activator.

The whitening cream is for example a gel which generally contains hydrogen peroxide. The activator is usually in powder form.

The two preparations are combined and mixed shortly before application on the skin to activate hydrogen peroxide.

Generally, the user mixes the preparations described above with a tool such as a plastic spatula, in a particular ratio, in a bowl. Then, the user applies the mixture uniformly on his/her face. This manual process is tedious and inconvenient.

Moreover, the accuracy of the dosing is limited. This can be detrimental, as the proper mixing and dosing of the two preparations directly affects the release of active oxygen from the mixture and hence, the efficiency of the whitening.

In some cases, improper mixing or inappropriate proportions of oxidizing preparation and activator may lead the user to use unsafe concentrations of oxidant and/or activator. At higher concentration of oxidant (which is usually very active) and/or activator (which is usually an alkaline material), the mixture may be corrosive to skin.

One aim of the invention is to obtain a kit which allows a safe and efficient whitening of the skin of the user, and which is still convenient to use.

Accordingly, the subject-matter of the invention is a kit as defined above, comprising:

- an oxidizing composition application device;
- wherein the kit comprises an activator sheet which is movable independently of the oxidizing composition application device, the activator sheet comprising an outer deformable substrate intended to be applied on an oxidizing composition placed on the skin of the user, the activator sheet comprising an activator composition carried by the outer substrate.

The kit according to the invention may comprise one or more of the following feature(s), taken in isolation, or according to any one of any technically feasible combination:

- the outer substrate comprises at least one fibrous layer;
- the outer substrate comprise at least one film layer laminated of the fibrous layer;
- the activator composition is a solid, in particular a powder, carried by the outer substrate;
- the activator composition comprises a base, such as an alkali salt, in particular sodium hydroxide or potassium hydroxide, ammonia, an amine, such as triethanolamine, a carbonate, a gluconate, a peroxide, an aminoacid and their salts, a zeolite, a silicate, or mixtures thereof;
- the activator sheet comprises a binder, in particular a water soluble binder, attaching the activator composition to the outer substrate, the binder advantageously comprising a water soluble polymer, such as a natural or synthetic water soluble polymer;
- the activator sheet is a face mask capable of defining at least one central through opening, intended to receive a nose of the user, and at least two upper through openings for placing in front of the eyes of the user;
- the oxidizing composition application device comprises an oxidizing sheet in particular an oxidizing mask, which is movable independently of the activator sheet, the oxidizing sheet comprising an inner substrate, intended to be applied against the body surface of the user and an oxidizing composition carried by the inner substrate;
- the oxidizing composition comprises a peroxide, a persulfate salt, a perborate salt, a carbonate salt, a percarbonate salt or mixtures thereof;
- the oxidizing composition is carried on the oxidizing sheet in a gel form, in an emulsion form, or in a liquid form;
- the oxidizing composition application device comprises a container containing the oxidizing composition and an applicator tool for applying the oxidizing composition on the body surface of the user;
- a packaging having a first compartment for receiving the oxidizing composition application device and a second compartment, sealingly separate from the first compartment, for receiving the activator sheet.

The invention also concerns a cosmetic treatment method for whitening a body surface of a user comprising the following steps:

providing a kit as above above;

applying a oxidizing composition on a body surface of the user, using the oxidizing composition application device;

placing the activator sheet on the oxidizing composition applied on the body surface;

whitening the body surface located facing the activator sheet.

The method according to the invention may comprise one or more of the following feature(s), taken in isolation or according to any technical feasible combination:

the oxidizing composition application device comprises an oxidizing sheet carrying the oxidizing composition, the application step comprising applying the oxidizing sheet on the body surface of the user, the activator sheet being applied on the oxidizing sheet.

The invention also concerns a process for manufacturing a kit as defined above comprising the following steps:

providing a medium intended to become an outer substrate of an activator sheet;

spreading an activator composition on the medium;

attaching the activator composition on the medium;

obtaining an activator sheet from the medium comprising the activation composition;

providing an oxidizing composition application device.

The invention will be better understood, upon reading of the following description, taken solely as an example, and made in reference to the following drawings, in which.

Figure 1:
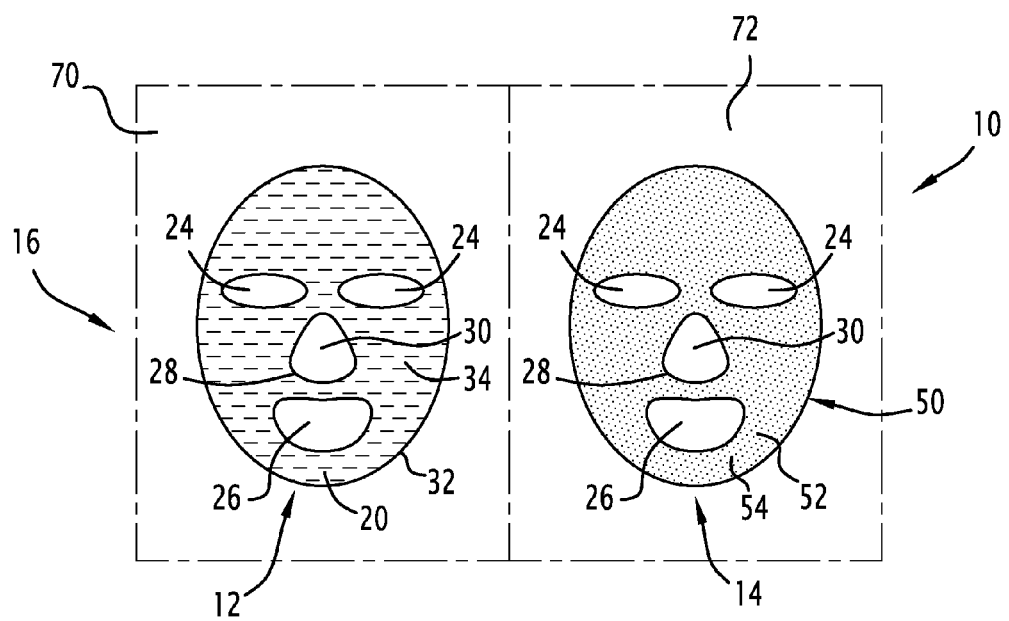
FIG. 1 is a schematic front view of a first kit according to the invention, before use.

A first kit 10 according to the invention is shown in FIG. 1. The first kit 10 comprises an oxidizing composition application device 12, and, according to the invention, an activation sheet 14, here in the form of a mask.

The activation sheet 14 is movable independently of the oxidizing composition application device 12.

The kit 10 advantageously comprises at least one packaging 16 containing the oxidizing composition application device 12 and/or the activator sheet 14.

Figure 2:
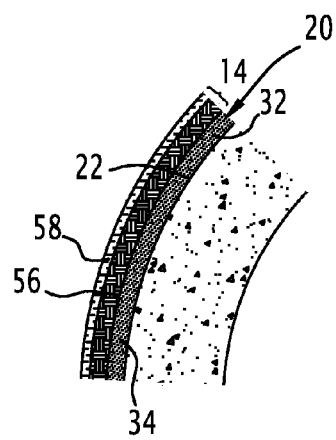
FIG. 2 is a partial cross section view of the first kit according to the invention, placed on the skin of a user.

In the embodiment of FIG. 1, the oxidizing composition application device 12 comprises an oxidizing sheet 20 intended to be applied on a body surface 22 of a user, which can be seen in FIG. 2.

The body surface 22 of the user is advantageously the skin of the user, in particular the skin located on a member of the user such as an arm or a leg, or preferably, the skin on the face of the user.

In a particular embodiment, the oxidizing sheet 20 is an oxidizing face mask. In this case, it has a rounded shape, for example a circular shape. Alternatively, the shape is polygonal.

Advantageously, it comprises at least two through openings 24 intended to be placed facing the eyes of a user, and another through opening 26 intended to be placed facing the mouth of a user.

The mask also comprises a slit 28 delimiting a flapper 30 intended to be pushed away by the nose of the user, to delimit a nose insertion through opening.

In a variant, the slit 28 delimits a through opening without flapper 30.

The oxidizing sheet 20 is deformable to the touch, to adapt to the conformation of the body surface 22.

It comprises a flat inner substrate 32 and an oxidizing composition 34 carried by the flat inner substrate 32.

Advantageously, the inner substrate 32 is water insoluble. By «water insoluble», it is meant that the inner substrate 32 does not dissolve or readily break apart upon immersion in water.

Advantageously, the inner substrate 32 comprises at least a fibrous layer. It can be in the form of woven, knitted, nonwoven or/and a polymeric mesh.

Advantageously, the substrate comprises a fibrous layer non-woven fibers. In a preferred embodiment, the inner substrate 32 is made of a non-woven.

By "non-woven", it is meant, in the sense of this invention, a substrate including fibers in which the individual fibers or filaments are arranged in a disordered manner in a sheet-like structure and which are neither woven nor knit. The fibers of the nonwoven body are generally linked to one another, under the effect of a mechanical action (for example, by needle-punching, air jet, water jet, etc.), or under the effect of a thermal action, or by adding a binder.

Such a non-woven material is, for example, defined by standard ISO 9092, as a web or a sheet of fibers oriented directionally or at random, bound by friction and/or cohesion and/or adhesion, excluding paper or products obtained by weaving, knitting, tufting or stitching incorporating threads or bonding filaments.

A non-woven material differs from a paper by the length of the fibers used. In paper, the fibers are shorter. However, there are nonwoven materials based on cellulose fibers that are produced by wet process and have short fibers as in paper. The difference between a nonwoven material and a paper is generally the absence of a hydrogen bond between the fibers in a nonwoven material.

The fibers of the substrate 32 can be natural fibers, synthetic fibers or mixtures thereof. Non limiting examples of synthetic fibers are Polyester, Polyolefin (Polypropylene. Polyethylene), Polyamide (Nylon 6, Nylon 66), Viscose, Acrylic fibers, Modacrylic fibers, Poly vinylidene chloride and Spandex.

Example of natural fiber include cellulosic fibers (such as wood pulp, cotton, hemp, jute, and flax fibers), silk, and keratin (such as wool and camel hair fibers).

The size and shape of the inner substrate depends on the nature of the product. For example, an inner substrate 32 adapted to fit the face of a user may have a surface area ranging from 0.25 $cm^2$ to 500 $cm^2$, preferably from 200 $cm^2$ to 450 $cm^2$. The substrate 32 typically has a density of 30 $g/m^2$ to 400 $g/m^2$, preferably 40 $g/m^2$ to 80 $g/m^2$.

The oxidizing composition 34 is carried by the inner substrate 32.

In a preferred embodiment, the oxidizing composition 34 impregnates the inner substrate 32. The degree of impregnation is for example between 100% in mass to 800% in mass relative to the mass of the inner substrate 32, preferably between 100% in mass to 500% in mass and even more preferably between 300% in mass and 400% in mass.

In one embodiment of the invention, the substrate 32 can be composed of another layer of a thin film at underside are to be avoided from whitening. For examples, if substrate 32 is in the shape of mask, it can be comprised of a film over the eye in order to avoid the whitening of eyebrows.

The oxidizing composition 34 is for example in the form of a liquid or of a gel form.

In particular, the oxidizing composition 34 can be in the form of an aqueous gel or an aqueous dispersion or emulsion (oil-in-water or water-in-oil), or an oil-based gel such as an anhydrous silicone or a non-silicone based gel.

Suitable aqueous gels contain from about 0.1% in mass to 99% in mass of water in particular between 70% in mass to 80% in mass of water. It contains from about 1% in mass to 99.9% in mass of other cosmetic ingredients including at least an oxidizing compound, preferably between 20% in mass to 30% in mass of these ingredients.

Emulsions (oil-in-water or water-in-oil) comprise from about 0.1% in mass to 99% in mass, preferably between 60% in mass to 80% in mass of water and from about 0.1% in mass to 99% in mass, and preferably between 20% in mass to 40% in mass of oil and other ingredients.

Among the other ingredients, the oxidizing composition 34 comprises at least one oxidizing compound. The oxidizing compound is for example chosen among a peroxide, a persulphate, a perborate, a percarbonate or mixtures thereof.

Peroxide oxidizing compounds are for example hydrogen peroxide, calcium peroxide and mixtures thereof. Persulfate oxidizing compounds are for example alkali metal persulfate, alkaline earth metal persulphate and mixtures thereof. Perborate oxidizing compounds are for example alkali metal perborate, alkaline earth metal perborate, ammonium perborate and mixtures thereof. Examples of percarbonate oxidizing compounds are alkali metal percarbonates, alkaline earth metal percarbonates and mixtures thereof.

The mass content of oxidizing compounds in the oxidizing composition ranges from 0.1% in mass to 30% in mass, preferably from 1% in mass to 15% in mass, more preferably from 2% in mass to 7% in mass.

The pH of the oxidizing composition 34 is acid. It ranges from 2 to 6, and preferably from 3 to 5.

Accordingly, the oxidizing composition 34 may comprise an acid, such as phosphoric acid.

Advantageously, the oxidizing composition 34 also contains one or more stabilizers.

Examples of stabilizers are disodium phosphate, acetaminophen, hydroxyquinoline sulfate, salicylic acid, editronic acid, tetrasodium iminodisuccinate and phenacetin.

In one embodiment of the invention, the oxidizing composition 34 is in the form of an emulsion comprising water, primary oils, and emulsifiers to be used in a water-in-oil emulsion or in a oil-in-water emulsion.

In this example, the primary oil can be a silicone oil, a petroleum oil, and mixtures thereof.

Examples of emulsifiers are nonionic surfactants such as glyceryl stearate, cetearyl alcohol, cetyl palmitate, cocoglycerides, ceteareth-33, cereareth-12, ceteareth 33, linear and/or branched chain stearyl and or cetostearyl steareths, cetearyl alcohol, hydrophobically modified siloxanes, hydrophilically modified siloxanes, linear or branched chain monosorbates, linear or branched chain polysorbates; sorbitan monostearates and sorbitan polysorbates and mixtures thereof.

Other anionic or cationic surfactants can also be used.

In some cases, in particular when the oxidizing composition 34 is a gel, it comprises at least a thickening agent. Examples of thickening agents are cationic, anionic or non-ionic in nature. Water phase thickening agents examples are inorganic or organic compounds such as aluminum hydroxide, magnesium silicates, aluminum magnesium silicates, cellulose derivatives (methyl cellulose, methyl ethyl cellulose), plant derived hydrocolloids (alginates, propylene glycol alginate, carrageenates), starch derivatives, tragant, slats of polyacrylic acids and polyvinyl alcohols.

According to the invention, the activator sheet 14 is intended to be placed on the oxidizing composition 34 applied on the body surface 22. It has preferably the shape of a face mask, similar to the face mask of the oxidizing sheet 20 described above.

The activator sheet 14 comprises a flat deformable outer substrate 50, an activator composition 52, preferably in the form of a powder, and a binder 54 attaching the activator composition 52 to on the outer substrate 50.

The outer substrate 50 has a structure similar to that of the inner substrate 32. It comprises at least one fibrous layer 56, preferably in the form of woven, knitted, nonwoven or a polymeric mesh.

Preferably, the fibrous layer 56 is a non-woven as described above.

In an embodiment shown in FIG. 2, the outer substrate 50 further comprises a film layer 58 laminated on the fibrous layer 56.

The fibrous layer 56 preferably contains synthetic fibers such as PET or PE fibers.

The mass percent of synthetic fibers in the outer substrate 50 ranges from 1% to 100%, preferably from 70% to 100%.

The film layer 58 is for example continuous. It may be breathable such as permeable to water vapor and gases.

On the contrary, it can be impervious to gases.

In an example of breathable film, the film is made of a polymer such as polyvinyl alcohol (PVOH), polyvinyl acetate (PVA), ethylene vinyl alcohol (EVA), polyurethane, ethylene methylacrylate (EMA) and ethylene methylacrylic acid (EMM).

Example of impervious films are polyolefin films, such as polyethylene and polypropylene films.

The film layer 58 is advantageously laminated on the fibrous layer 56 in order to be placed opposite the oxidizing composition application device 12. This maximizes the transfer of free oxygen generated in the oxidation composition application device 12 towards the body surface 22.

The activator composition 52 preferably comprises an activator solid powder. By «activator», it is meant herein a chemical substance which favors the decomposition of the oxidizing compound available in the oxidizing composition 34.

The activator is chosen among a base such as an alkali salt, in particular sodium hydroxide or potassium hydroxide, ammonia, an amine such as triethanol amine, a carbonate, a gluconate, a peroxide, an amino acid and their salts, a zeolite, a silicate, or mixtures thereof.

Examples of activators are chosen among, basic compounds, such as sodium hydroxide potassium hydroxide, or calcium hydroxide, ammonia, carbonates, bicarbonates such as sodium bicarbonate or guanidine carbonate, halogen salts, such as sodium chloride, gluconates such as sodium manganese gluconate, borates such as sodium borate, peroxides, such as calcium peroxide, basic amino acids and their salts such as lysine, arginine and salts thereof, potassium, or urea, amines and derivatives such as aminomethylpropanol, aminopropanol, monoethanolamine (MEA) or triethanolamine, aminopropyltriethoxysilane (APT), silicates, in particular derivatives of sodium silicate or magnesium silicate, including laponite (in particular Laponite XLG, commercialized by the company Rockwood), smectites for example, metasilicate of sodium hecorite, zeolites, such as zeolite Zeochem commercialized by the company under the X-MOL reference, or their mixtures.

Advantageously, the activators are selected from sodium bicarbonate, laponite, zeolites, calcium peroxide, sodium hydroxide (preferably to 10% in mass in water), sodium metasilicate and mixtures thereof.

The binder 54 is for example a water soluble binder, in particular a water soluble polymer. Water soluble polymers can be chosen among natural water soluble polymers or synthetic water soluble polymers.

Examples of natural water soluble polymers are vegetable starches, casein and gelatin. Examples of synthetic water soluble polymer are polyacrylamides, polyvinylalcohol, polyacrylic acid, polyamines, polyethyleneimines, polyvinylpyrrolidone copolymers (PVP), polyethylene glycols, methylcellulose derivatives, quaternary ammonium cellulose, carboxymethyl cellulose, xanthan, pectin, guar gum derivatives and carboxypolymethylene or their mixtures.

In a particular example, the mass content of water soluble polymer in the aqueous solution is between 1% in mass to 70% in mass, for example between 5% in mass to 50% in mass, and more preferably between 5% in mass to 30% in mass, relative to the total mass of aqueous solution.

The density of the outer substrate 50 is for example comprised between 30 g/m$^2$ and 150 g/m$^2$, advantageously from 40 g/m$^2$ to 100 g/m$^2$, and more preferably from 50 g/m$^2$ to 60 g/m$^2$.

The binder 54 has a density between 5 g/m$^2$ to 30 g/m$^2$ more specifically from 6 g/m$^2$ to 25 g/m$^2$, and more preferably between 7 g/m$^2$ and 20 g/m$^2$.

Activator composition 52 has a surface density of between 15 g/m$^2$ to 70 g/m$^2$, more specifically between 20 g/m$^2$ to 50 g/m$^2$ and even more specifically from 25 g/m$^2$ to 40 g/m$^2$.

When coated by the activator composition 52 and by the binder 54, the activator sheet 14 is between 50 g/m$^2$ to 250 g/m$^2$, more specifically from 70 g/m$^2$ to 140 g/m$^2$ and even more specifically from 90 g/m$^2$ to 110 g/m$^2$.

In the example of FIG. 1, the packaging 16 comprises at least a first compartment 70 containing the oxidizing composition application device 12 and at least a second compartment containing the activator sheet 14.

The compartments 70, 72 are sealingly separated.

In an alternate embodiment, the kit 10 according to the invention comprises two different packaging 24, each delimiting a compartment 70, 72.

According to the invention, the activator sheet 14 is movable independently of the oxidizing composition application device 12. In particular, the application device 12, for example in form of an oxidizing sheet 20, can be placed on a body surface 22 of the user, before placing the activator sheet 14.

The activator sheet 14 can hence be placed on the oxidizing composition 34, after application of the oxidizing composition 34 on the body surface 22 of the user.

Figure 3:
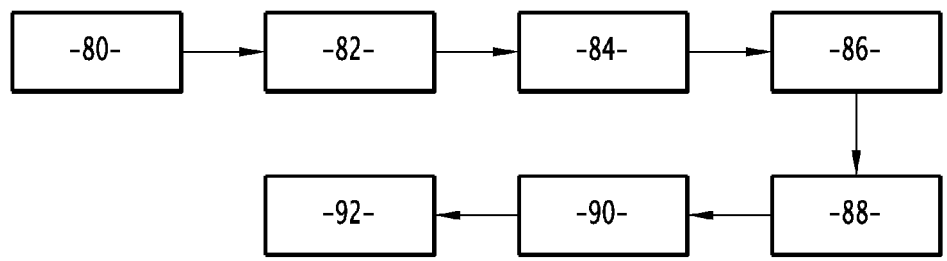
FIG. 3 is a functional flow chart of some steps of a process for manufacturing a kit according to the invention.

A process for manufacturing the activator sheet 14 of a kit 10 according to the invention is shown schematically in FIG. 3.

This process comprises providing a medium intended to form an outer substrate 50 of the activator sheet 14, such as a roll of material having as the same structure and composition as the outer substrate 50.

In a first step 80 of the manufacturing process, the medium is unwinded.

In a second step 82, binder 54 is sprayed on the medium, for example by nozzles, having a diameter preferably between 200 microns to 100 microns.

In a further step 84, the activator composition 52, in form of a powder, is scattered evenly on the medium. For example, the medium passes underneath a powder scattering head at a uniform speed by means of a conveyor such as a conveyor belt.

Advantageously, the activator composition 52 is led through a hopper onto a roller. A doctor blade, spring biased to the roller, strikes the excess powder from the roller.

An oscillating brush brushes off the powder from the scattering roller.

To guarantee a uniform spreading of powder as well as the breaking up of lumps of powder, the powder falls non-contacting through one or more oscillator distributor sieves onto the medium.

At step 86, the medium, onto which the activator composition 52 and the binder 54 have been applied, is quickly dried. The drying temperature is chosen to be below the melting and/or burning temperature of the medium and of the activator composition 52.

In the optional step 88, the medium can be rolled again in a winding unit. At step 90, the medium, coated with the activator composition 52 attached to the medium by the binder 54, is cut into a substrate shape by a cutting unit.

In step 92, an activator sheet 14 such as an activator mask is obtained.

Similarly, the oxidizing sheet 20 is manufactured by impregnating a second medium of structure and composition identical to the structure and composition of the inner substrate 32 with an oxidizing composition 34, followed by cutting the impregnated medium to the shape of an oxidizing sheet 20, such as an oxidizing mask.

The sheets 14, 20 are then packed into the packaging 16.

A cosmetic treatment method according to the invention, using the first kit 10, will be now described.

In a first step, the user opens the compartment 70 and grabs the oxidizing sheet 20. The user then places the oxidizing sheet 20 in contact with the body surface 22. The oxidizing composition 34 carried by the inner substrate 32 spreads on the body surface 22

Subsequently, the user opens the second compartment 72 and grabs the activator sheet 14. The user then applies the applicator sheet 14 onto the oxidizing composition 34 carried by the oxidizing sheet 20, opposite the face of the oxidizing sheet 20 in contact with the body surface 22.

The activator composition 52 available at the surface of the activator sheet 14 reacts with the oxidizing composition 34 to produce oxygen which is confined towards the body surface 22.

In the particular embodiment of FIG. 2, in which the activator sheet 14 comprises an outer film 58, the oxygen produced by the reaction of the activator with the oxidizing composition is guided towards the body surface 22 by the film 58.

A very efficient whitening effect is therefore obtained on the body surface 22.

Moreover, no manual dosing of oxidizing composition 34 or activator composition 52 has to be made by the user.

The user merely places the oxidizing sheet 20 carrying the oxidizing composition 34 on the body surface 22, and then the activator sheet 14 on the oxidizing sheet 20.

The use of the kit 10 according to the invention is therefore easy and safe. The risk of having inappropriate concentrations of oxidizing composition 34 or of activator composition 52 is greatly diminished.

Figure 4:
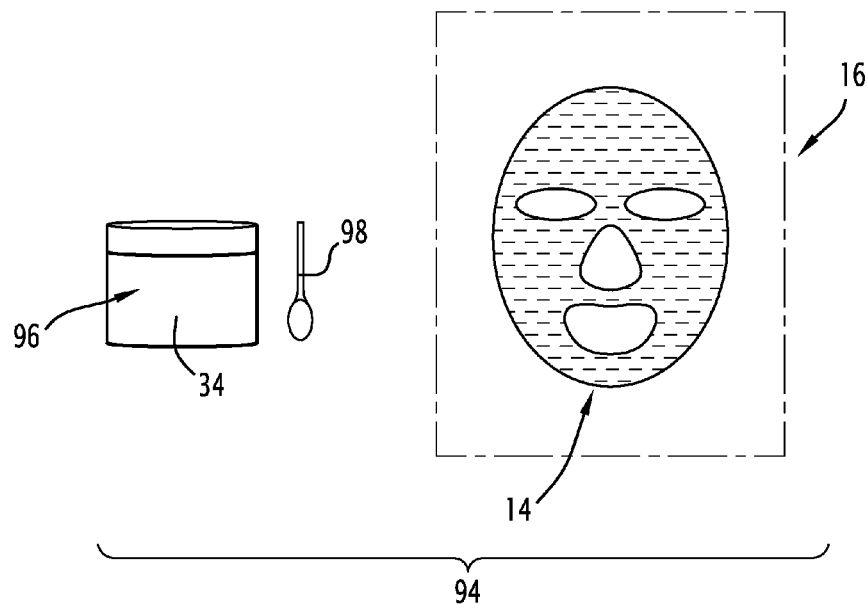
FIG. 4 is a view similar to FIG. 1, illustrating a second kit according to the invention.

In a second kit 94 according to the invention, shown in FIG. 4, the oxidizing composition application device 12 comprises a container 96 containing the oxidizing composition 34 and a tool 98 for applying the composition 96 in the container 96 to the body surface 22 of the user.

The activator sheet 14 is contained in a packaging 16. The operation of the second kit 94 according to the invention differs from that of the first kit 10 by the fact that the user applies the oxidizing composition 34 with the tool 98, by sampling the composition in the container 96.

The activator sheet 14 is then placed on the body surface 22 covered with oxidizing composition 34.

In another variant, the activator sheet 14 and/or the oxidizing sheet 20 are patches, without any through-holes or slits made through.

The patches are for example polygonal in shape or rounded in shape such as circular or elliptic.

The patches may be applied on a body surface which is different than the face of the user, such as the members of the user, e.g. the arms or legs of the user.

Specific examples of kits according to the invention will be now described.

EXAMPLE 1

A kit 10 according to the invention is a dual sachet mask, where the oxidizing sheet 20 and the activator sheet 14 are cut in to the shape of face masks to be used for instant whitening of the face.

During the application, the user first applies the oxidizing mask 20 on the face and the activator mask 14 over the oxidizing mask 20 for a specific period of time.

Oxidizing Mask 20

The substrate 32 of the oxidizing mask 20 is composed of 100% viscose fiber. The surface density of the inner substrate 32 is 50 g/m2. This substrate 50 was impregnated with an hydrogen peroxide based oxidizing composition 34. The level on impregnation of on the inner substrate 32 was 500% of the weight of the inner substrate 32.

Examples of oxidizing composition are as follows:
(A) Emulsion Oxidizing Composition

| Ingredient | % |
|---|---|
| Water | 83.59 |
| Hydrogen Peroxide (50%) | 12.00 |
| Trideceth 2 Carboxamide MEA | 0.85 |
| Cetaryl alcohol & Ceteareth 25 | 2.85 |
| Tetrasodium Pyrophosphate | 0.02 |
| Sodium Stannate | 0.04 |
| Phosphoric Acid | 0.10 |

(B) Gel Oxidizing Composition

| Ingredient | % |
|---|---|
| Water | 85.32 |
| Polyquarternium 37 | 2.5 |
| Hydrogen peroxide (50%) | 12.0 |
| Tetrasodium pyrophosphate | 0.02 |
| Sodium Stannate | 0.04 |
| Phosphoric Acid | 0.12 |

(C) Liquid Oxidizing Composition

| Ingredient | % |
|---|---|
| Water | 90.14 |
| Hydrogen Peroxide (50%) | 10.0 |
| Tetrasodium pyrophosphate | 0.018 |
| Sodium Stannate | 0.038 |
| Phosphoric Acid | 0.12 |

Activator Mask 14

The outer substrate 50 of the activator mask 14 is composed of PET fiber, coated with potassium persulfate using PVP binder of 10% concentration. The surface density of the substrate is 50 g/m$^2$. The substrate was coated with 30 g/m$^2$ of potassium persulfate.

Testing

Efficiencies of the kit according to the invention is evaluated by patch test. The following three applications were done on 2×2 inches area of an arm of a user.

Application P: a topical application of oxidizing composition (0.45 g) and activator powder (0.06 g) previously mixed together was done.

Application Q: The oxidizing composition (0.45 grams) was applied topically and the activator mask 14 described above was applied over it.

Application R: The oxidizing mask 20 impregnated with 1 g of oxidizing composition was applied on the skin and the activator mask 14 described above was applied over it.

The L value (withtness) of the skin was measured using a spectrophotometer according to Standard after 15 minutes of the application and then after every 15 minutes for the next one hour.

Figure 5:
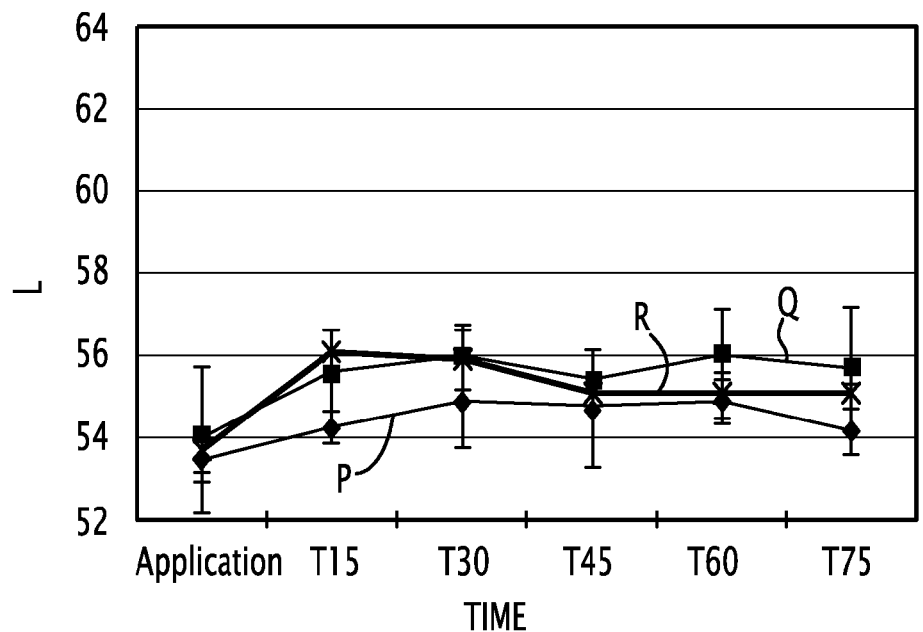
FIGS. 5 and 6 are graphs showing the efficiency over time of two examples of kits according to the invention.

The results are shown in FIG. 5. This figure clearly show that when patches of activator mask 14 i.e. application Q or patches of activator mask 14 and oxidizing mask 50 are used, the value of L obtained after 15 minutes of application (T15) was higher than for topical application P after 45 and 60 minutes the value of L becomes similar in all three applications.

EXAMPLE 2

A kit 10 according to the invention is a dual sachet mask, where the oxidizing sheet 20 and the activator sheet 14 are cut in to the shape of face mask to be used for instant whitening of the face.

During the application, the user first applies the oxidizing mask 20 on the face and the activator mask 14 over the oxidizing mask 20 for a specific period of time.

Oxidizing Mask 20

The oxidizing mask 20 is composed of a similar substrate 32 and oxidizing composition described in example 1.

Activator Mask 14

The substrate of the activator mask 14 is composed of 96% in mass cellulosic fibers and 4% in mass PE fibers and laminated with a PE film of 50 microns. The mask was coated with 30 g/m$^2$ potassium per sulfate.

Testing

A similar patch test as described in Example 1 was performed with the following applications.

Application S was a topical application of product where oxidizing composition (0.45 g) and activator powder (0.06 g) were mixed together.

Application T: The oxidizing composition (0.45 g) was applied topically and activation mask 14 described in the invention was applied over it.

Application U: Oxidizing mask 20 impregnated with 1 gr of oxidizing composition was applied on the skin and activation mask 14 was applied over it.

Figure 6:
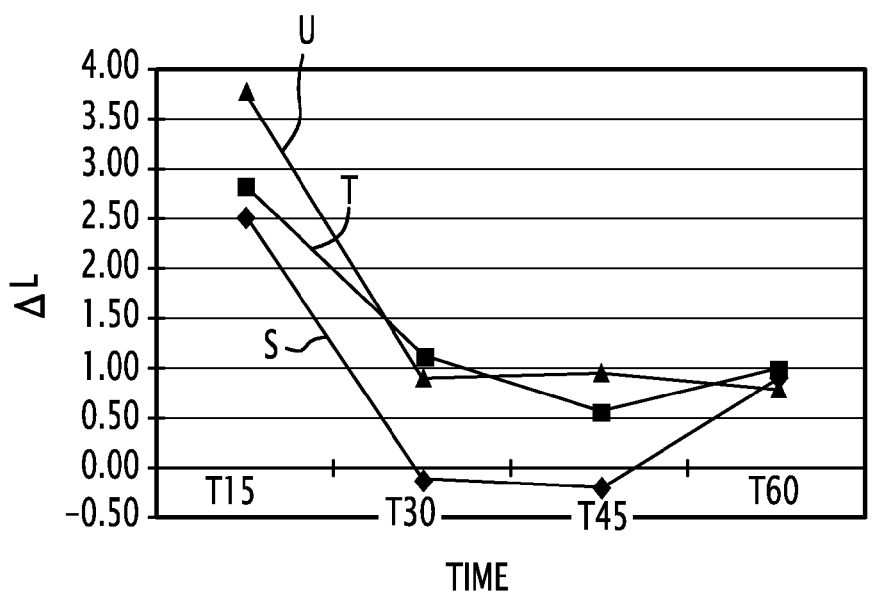

FIG. 6 shows that use of a laminated non-woven as an activator mask 14 enhances the instant whitening effect, with a higher value of ΔL.

The invention claimed is:

1. A kit for whitening a body skin surface of a user, comprising:
   an oxidizing composition application device;
   an activator sheet which is movable independently of the oxidizing composition application device, the activator sheet comprising an outer deformable substrate intended to be applied on an oxidizing composition placed on the skin of the user, the activator sheet comprising an activator composition carried by the outer substrate;
   wherein the oxidizing composition application device comprises an oxidizing sheet, which is movable independently of the activator sheet, the oxidizing sheet comprising an inner substrate, intended to be applied against the body surface of the user and an oxidizing composition carried by the inner substrate.

2. The kit according to claim 1, wherein the outer substrate comprises at least one fibrous layer.

3. The kit according to claim 2, wherein the outer substrate comprise at least one film layer laminated on the fibrous layer.

4. The kit according to claim 3, wherein the activator composition is a solid, carried by the outer substrate.

5. The kit according to claim 3, wherein the activator sheet comprises a binder attaching the activator composition to the outer substrate.

6. The kit according to claim 2, wherein the activator composition is a solid, carried by the outer substrate.

7. The kit according to claim 2, wherein the activator sheet comprises a binder attaching the activator composition to the outer substrate.

8. The kit according to claim 2, wherein the activator sheet is a face mask capable of defining at least one central through opening, intended to receive a nose of the user, and at least two upper through openings for placing in front of the eyes of the user.

9. The kit according to claim 1, wherein the activator composition is a solid, carried by the outer substrate.

10. The kit according to claim 9, wherein the activator composition comprises a base, ammonia, an amine, a carbonate, a gluconate, a peroxide, an aminoacid and their salts, a zeolite, a silicate, or mixtures thereof.

11. The kit according to claim 10, wherein the activator sheet comprises a binder attaching the activator composition to the outer substrate.

12. The kit according to claim 9, wherein the activator sheet comprises a binder attaching the activator composition to the outer substrate.

13. The kit according to claim 1, wherein the activator sheet comprises a binder, attaching the activator composition to the outer substrate.

14. The kit according to claim 1, wherein the activator sheet is a face mask capable of defining at least one central through opening, intended to receive a nose of the user, and at least two upper through openings for placing in front of the eyes of the user.

15. The kit according to claim 1, wherein the oxidizing composition comprises a peroxide, a persulfate salt, a perborate salt, a carbonate salt, a percarbonate salt or mixtures thereof.

16. The kit according to claim 1, wherein the oxidizing composition is carried on the oxidizing sheet in a gel form, in an emulsion form, or in a liquid form.

17. The kit according to claim 1, comprising a packaging having a first compartment for receiving the oxidizing composition application device and a second compartment, sealingly separate from the first compartment, for receiving the activator sheet.

18. A cosmetic treatment method for whitening a body skin surface of a user comprising the following steps:
    providing a kit according to claim 1, said kit comprising an oxidizing sheet including an oxidizing composition and an activator sheet including an activator composition;
    applying the oxidizing sheet on a body skin surface of the user;
    placing the activator sheet on the oxidizing sheet applied on the body skin surface;
    whitening the body skin surface located facing the activator sheet.

19. A process for manufacturing a kit according to claim 1, comprising the following steps:
    providing a medium intended to become an outer substrate of an activator sheet;
    spreading an activator composition on the medium;
    attaching the activator composition on the medium;
    obtaining an activator sheet from the medium comprising the activation composition;
    providing an oxidizing composition application device.

20. The process according to claim 19, comprising a step of applying a binder prior to spreading the activator composition, the process comprising, after spreading the activator composition, drying the binder to attach the activator composition on the medium.

* * * * *